(12) United States Patent
Hei et al.

(10) Patent No.: US 6,855,328 B2
(45) Date of Patent: Feb. 15, 2005

(54) ANTIMICROBIAL AND ANTIVIRAL COMPOSITIONS CONTAINING AN OXIDIZING SPECIES

(75) Inventors: Robert D. P. Hei, Baldwin, WI (US); Francis L. Richter, Lino Lakes, MN (US); Duane Joseph Reinhardt, Maplewood, MN (US); Brian R. Leafblad, St. Paul, MN (US)

(73) Assignee: Ecolab Inc., St. Paul, MN (US)

( * ) Notice: Subject to any disclaimer, the term of this patent is extended or adjusted under 35 U.S.C. 154(b) by 179 days.

(21) Appl. No.: 10/109,806

(22) Filed: Mar. 28, 2002

(65) Prior Publication Data

US 2003/0185902 A1 Oct. 2, 2003

(51) Int. Cl.$^7$ ............... A01N 59/00; A01N 59/12; A01N 33/00; A01N 37/00

(52) U.S. Cl. ............... 424/405; 424/400; 424/76.1; 424/76.8; 424/600; 424/661; 424/663; 424/667; 424/669; 424/723

(58) Field of Search ............... 424/400, 405, 424/76.1, 76.8, 600, 661, 663, 667, 669, 723

(56) References Cited

U.S. PATENT DOCUMENTS

| | | |
|---|---|---|
| 2,193,636 A | 3/1940 | Marshall |
| 2,512,640 A | 6/1950 | Greenspan et al. |
| 2,662,855 A | 12/1953 | Kamlet |
| 2,666,010 A | 1/1954 | Stayner |
| 2,679,533 A | 5/1954 | Darragh et al. |
| 2,692,231 A | 10/1954 | Stayner et al. |
| 2,740,744 A | 4/1956 | Abramitis et al. |
| 2,746,928 A | 5/1956 | Darragh et al. |
| 2,751,713 A | 6/1956 | Abramitis |
| 2,863,798 A | 12/1958 | Shelanski et al. |
| 2,868,686 A | 1/1959 | Shelanski et al. |
| 2,917,428 A | 12/1959 | Hitzman |
| 3,152,073 A | 10/1964 | Morton |
| 3,194,758 A | 7/1965 | Lissant |
| 3,223,643 A | 12/1965 | Law |
| 3,344,018 A | 9/1967 | Shibe, Jr. et al. |
| 3,380,923 A | 4/1968 | Beach |
| 3,525,696 A | 8/1970 | Schmidt et al. |
| 3,749,673 A | 7/1973 | Jones et al. |
| 3,778,476 A | 12/1973 | Rembaum et al. |
| 3,898,336 A | 8/1975 | Rembaum et al. |
| 3,958,020 A | 5/1976 | deVries |
| 3,966,090 A | 6/1976 | Prussin et al. |
| 4,045,358 A | 8/1977 | Ramachandran |
| 4,051,058 A | 9/1977 | Bowing et al. |
| 4,051,059 A | 9/1977 | Böwing et al. |
| 4,073,888 A | 2/1978 | Snyder |
| 4,111,679 A | 9/1978 | Shair et al. |
| 4,113,857 A | 9/1978 | Shetty |
| 4,131,556 A | 12/1978 | Klopotek et al. |
| 4,144,211 A | 3/1979 | Chamberlin et al. |
| 4,187,183 A | 2/1980 | Hatch |
| 4,190,529 A | 2/1980 | Hatch |
| 4,206,233 A | 6/1980 | Quinlan |
| 4,336,152 A | 6/1982 | Like et al. |
| 4,397,757 A | 8/1983 | Bright et al. |
| 4,408,001 A | 10/1983 | Ginter et al. |
| 4,420,590 A | 12/1983 | Gartner |
| 4,592,488 A | 6/1986 | Simon et al. |
| 4,594,392 A | 6/1986 | Hatch |
| 4,597,975 A | 7/1986 | Woodward et al. |
| 4,654,208 A | 3/1987 | Stockel et al. |
| 4,704,212 A | 11/1987 | Schindler et al. |
| 4,737,307 A | 4/1988 | Brown et al. |
| 4,741,851 A | 5/1988 | Borrello |
| 4,804,492 A | 2/1989 | Bernarducci |
| 4,822,513 A | 4/1989 | Corby |
| 4,824,867 A | 4/1989 | Smith et al. |
| 4,857,223 A | 8/1989 | Borrello |
| 4,874,788 A | 10/1989 | Smith et al. |
| 4,900,721 A | 2/1990 | Bansemir et al. |
| 4,937,072 A | 6/1990 | Kessler et al. |
| 4,941,989 A | 7/1990 | Kramer et al. |
| 4,960,590 A | 10/1990 | Hollis et al. |
| 4,976,874 A | 12/1990 | Gannon et al. |
| 5,047,164 A | 9/1991 | Corby |
| 5,070,105 A | 12/1991 | Segall et al. |
| 5,081,106 A | 1/1992 | Bentley et al. |
| 5,093,078 A | 3/1992 | Hollis et al. |
| 5,117,049 A | 5/1992 | Venturello et al. |
| 5,141,652 A | 8/1992 | Moore, Jr. et al. |
| 5,200,189 A | 4/1993 | Oakes et al. |
| 5,202,047 A | 4/1993 | Corby |
| 5,229,072 A | 7/1993 | Tarancon |
| 5,264,191 A | 11/1993 | Nakao et al. |
| 5,314,968 A | 5/1994 | Frommer et al. |
| 5,320,805 A | 6/1994 | Kramer et al. |
| 5,366,983 A | 11/1994 | Lattin et al. |
| 5,389,384 A | 2/1995 | Jooste |
| 5,443,849 A | 8/1995 | Corby |

(List continued on next page.)

FOREIGN PATENT DOCUMENTS

| | | |
|---|---|---|
| DE | 18 13 584 | 10/1969 |
| DE | 28 21 199 | 11/1978 |

(List continued on next page.)

OTHER PUBLICATIONS

Abdelkader, M. et al., "Spectrophotometric Analysis of Quaternized Drugs", *Die Pharmazie*, vol. 35pp. 30–32 (1980).

(List continued on next page.)

*Primary Examiner*—Thurman K. Page
*Assistant Examiner*—Simon J. Oh
(74) *Attorney, Agent, or Firm*—Merchant & Gould P.C.

(57) ABSTRACT

An improved antimicrobial composition is described as a liquid concentrate. The liquid concentrate includes a complex resulting from an in-situ reaction of a cation source, an oxidant, a halide source having at least one iodine atom, and a non-mineral acid, or a mixture of a non-mineral acid to about 50% of a hydrophilic solvent by volume.

42 Claims, No Drawings

U.S. PATENT DOCUMENTS

| | | | |
|---|---|---|---|
| 5,545,349 A | 8/1996 | Kurii et al. | |
| 5,576,282 A | 11/1996 | Miracle et al. | |
| 5,620,527 A | 4/1997 | Kramer et al. | |
| 5,658,467 A | 8/1997 | LaZonby et al. | |
| 5,683,724 A | 11/1997 | Hei et al. | |
| 5,756,090 A | 5/1998 | Allen | |
| 5,858,117 A * | 1/1999 | Oakes et al. | 134/27 |
| 6,068,861 A | 5/2000 | Moore, Jr. et al. | |
| 6,106,854 A | 8/2000 | Belfer et al. | |
| 6,165,485 A | 12/2000 | Alther | |
| 6,251,386 B1 | 6/2001 | Johansen | |
| 6,258,765 B1 * | 7/2001 | Wei et al. | 510/224 |
| 2001/0009664 A1 | 7/2001 | Johansen | |

FOREIGN PATENT DOCUMENTS

| | | |
|---|---|---|
| DE | 29 05 373 | 9/1979 |
| DE | 29 05 373 A1 | 9/1979 |
| DE | 41 37 544 A1 | 5/1993 |
| EP | 0 086 423 A2 | 8/1983 |
| EP | 0 087 049 A1 | 8/1983 |
| EP | 0 095 377 A1 | 11/1983 |
| EP | 0 156 646 A1 | 10/1985 |
| EP | 0 185 970 A1 | 7/1986 |
| EP | 0 214 850 A2 | 3/1987 |
| EP | 0 443 640 A2 | 8/1991 |
| EP | 0 528 697 B1 | 2/1993 |
| EP | 0 832 964 A1 | 4/1998 |
| EP | 1 001 012 A1 | 5/2000 |
| FR | 2 663 852 A1 | 1/1992 |
| GB | 898820 | 6/1962 |
| GB | 1 265 919 | 3/1972 |
| GB | 1 301 861 | 1/1973 |
| GB | 1 346 594 | 2/1974 |
| GB | 2 132 087 A | 7/1984 |
| GB | 2 268 879 A | 1/1994 |
| JP | 4-082959 A | 3/1992 |
| JP | 4-107223 | 4/1992 |
| JP | 4-321627 A | 11/1992 |
| WO | WO 88/00795 | 2/1988 |
| WO | WO 88/02351 | 4/1988 |
| WO | WO 93/17693 | 9/1993 |
| WO | WO 94/00548 | 1/1994 |
| WO | WO 96/14092 | 5/1996 |
| WO | WO 97/34834 | 9/1997 |
| WO | WO 00/57703 | 10/2000 |
| WO | WO 00/57730 | 10/2000 |
| WO | WO 01/30946 | 5/2001 |

OTHER PUBLICATIONS

Arm. Khim. Zh., vol. 38, No. 1, pp. 53–57 (1985).

Baleux, B. et al., "Physicochimie Colloidale", *C.R. Acad. Sc. Paris*, pp. 1135–1137 (Apr. 4, 1966).

Chowdhury, A.N. et al., "Improved Rapid Determination of Nickel in Soils and Laterites", *Analytical Chemistry*, pp. 820–821 (Jun. 1960).

Darrow, R. et al., "An improved spectrophotometric triiodide assay for lipid hydroperoxides", *Chemical Abstracts*, vol. 121, No. 15, Abstract No. 121:174365e, pp. 546547 (Oct. 10, 1994).

Roberts et al., "Basic Principles of Organic Chemistry", 2nd Ed., pp. 1176, 1328 (1964).

"Chemical Abstracts", *The American Chemical Society*, vol. 121, No. 15, pp. 546–547 (Oct. 10, 1994).

60/056,622, provisional application filed Aug. 20, 1997.

U.S. Appl. No. 09/277,626, filed Mar. 26, 1999, Hei et al.

U.S. Appl. No. 09/277,592, filed Mar. 26, 1999, Hei et al.

Copy of International Search Report dated Feb. 20, 2004.

* cited by examiner

ANTIMICROBIAL AND ANTIVIRAL COMPOSITIONS CONTAINING AN OXIDIZING SPECIES

FIELD OF THE INVENTION

The invention relates to antimicrobial and antiviral compositions containing an oxidizing species. The materials are made by reacting cooperating ingredients at controlled proportions to form an oxidant that can have a variety of end uses. The oxidizing species of the invention is an in situ generated oxidant made stable as a non-aqueous or low aqueous liquid concentrate.

BACKGROUND OF THE INVENTION

A synergistic effect resulting from the combination of a source of quaternary or protonizable nitrogen, an oxidant, preferably peroxygen compound, and a halide source, for example, an elemental halogen(s), or metal or ammonium halide salt(s), preferably including an iodide salt has been reported in PCT Publication No. WO/00/057703. Since reaction is almost immediate, an in-situ aqueous or non-aqueous use solution can be available for use immediately after mixing as an antimicrobial or antiviral composition; or the active composition can be stabilized and post-incorporated into a non-aqueous liquid, gel, aerosol, powder, or solid formulation.

Aqueous, inorganic mineral acid-derived, halide salt stabilized, interhalide sanitizers for hard surface sanitizing are known.

SUMMARY OF THE INVENTION

We have now discovered that a stabilized combination of a cation source, an oxidant, and a halide source may be prepared and used as a clear liquid concentrate prior to dilution. This liquid concentrate does not require use of a mineral acid and is non-aqueous or low-aqueous. Accordingly, the invention resides in an antimicrobial liquid concentrate composition which includes a complex resulting from an in-situ reaction of a cation source, an oxidant, a halide source including a metal halide, a halogen or a mixture thereof, wherein said halide or halogen contains at least one iodine atom, and a non-mineral acid, or a mixture of a non-mineral acid to about 50% of a hydrophilic solvent by volume.

The invention also includes a sanitizing liquid concentrate composition which contains a cation source, preferably selected from a quaternary and protonizable nitrogen compound, an oxidant, preferably selected from a halogen containing oxidizer as $I_2$, $IO_3^-$, ICl, IBr, $IO_4^-$, BrCl, $Cl_2$, $OCl^-$, HOCl, $ClO_2^-$, $ClO_3^-$, $ClO_4^-$, $Br_2$, HOBr, $OBr^-$, $BrO_3^-$, and a mixture thereof, a halide source containing a metal halide, a halogen, or a mixture thereof, wherein said halide or halogen includes at least one iodine atom, and a non-mineral acid, or a mixture of a non-mineral acid and up to about 50% water by volume.

The invention also resides in the use of said concentrate to reduce microbial or viral populations on a surface or object or in a body or stream of water. Thus, this in-situ complex is effective in reducing microbial and viral populations on hard surfaces (such as glass, ceramics, metal, natural and synthetic rock, wood, and polymeric), elastomers and plastics, woven and non-woven substrates. More specifically, the compositions containing the complex are shown to be effective antimicrobial and antiviral agents for sanitizing and disinfecting surfaces and air streams typically encountered in hospital, surgical, infirmity, birthing, mortuary, and clinical diagnosis rooms. These surfaces can be those typified as "hard surfaces" (such as walls, floors, bed-pans, etc.), or woven and non-woven surfaces (such as surgical garments, draperies, bed linens, bandages, etc.), or patient-care equipment (such as respirators, diagnostic equipment, shunts, body scopes, etc.), or a plethora of surgical and diagnostic equipment.

The concentrate can also be used to reduce microbial or viral populations on animals or animal carcasses, bleaching of or reducing microbial or viral populations on woven or non-woven substrates, and treating skin diseases of, or on, mammals; i.e., in treating skin diseases on animals (especially mammals), or those which spread via transfer to air or surface substrates, such as disease from fungi, bacteria and viruses. The complex can also be used to reduce microbes in animal feeds, in animal watering stations and enclosures, in animal veterinarian clinics, animal surgical areas, and to reduce animal or human pathogenic (or opportunistic) microbes and viruses on animals. The complex can also be used to reduce opportunistic pathogenic microbes on living eggs.

Additionally, the compositions containing the complex are effective by themselves, or mixed with other adjuvants, in reducing microbial and viral populations in applications in the food industry. These include food preparation equipment, belt sprays for food transport lines, boot and hand-wash dip-pans, food storage facilities and anti-spoilage air circulation systems, aseptic packaging sanitizing, food refrigeration and cooler cleaners and sanitizers, warewashing sanitizing, blancher cleaning and sanitizing, food packaging materials, cutting board additives, third-sink sanitizing, beverage chillers and warmers, meat chilling or scalding waters, sanitizing gels, food processing antimicrobial garment sprays, and non-to-low-aqueous food preparation lubricants, oils, and rinse additives.

In a diluted form, this use solution will contain about 0.1 to 200,000 parts per million (ppm), preferably 5 to 10,000 ppm, and most preferably 10 to 100 ppm of the halide source.

The invention also resides in treating food processing or transport waters with said liquid, gel, solid, or powdered compositions.

The invention additionally resides in treating food processing equipment and/or ware, (e.g. utensils, dishware, washware,) with said liquid, gel, aerosol, solid, or powdered compositions, or solutions containing these compositions.

The invention additionally resides in sanitizing third-sink rinse waters and utensils (e.g. bar glasses) with said liquid, gel, solid, or powdered compositions.

The invention additionally resides in treating animal quarters, surgical or treatment areas, in animal feeds, or animal carcasses; with said compositions.

DETAILED DESCRIPTION OF THE INVENTION

The invention involves a complex for antimicrobial or antiviral use, including the product of the in-situ, i.e., in place, reaction of a source of a cation source, preferably a quaternary or protonizable nitrogen, an oxidant, preferably a halogen containing oxidizer or a peroxygen compound and, a halide or halogen source, e.g., a metal or ammonium halide salt; wherein the reaction is conducted in a low-aqueous, non-aqueous, gel, aerosol, solid phase or powdered media. Preferably, for each part by weight of the halide source there is about 1 to 10 parts by weight of a cation source, preferably a quaternary or protonizable nitrogen, and about 1 to 10 parts by weight of the oxidant, preferably halogen containing oxidizer or peroxygen compound. In an aqueous reacted solution, or in a use solution, the pH is about 9.5 or less.

The complex of the invention may be prepared as a liquid concentrate for storage and shipping prior to dilution at the site where it is to be used. In this aspect, the complex is prepared in a non-mineral acid, or a mixture of a non-mineral acid and up to about 50% of a hydrophilic solvent by volume to provide the liquid. The non-mineral acid may be, for example, one of the following: acetic, propionic, adipic, glycolic, lactic, succinic, citric, gluconic, glutaric, tartaric, organic sulfonic acid, or mixtures thereof. The organic sulfonic acids include, for example, aryl and alkylarylsulfonic acids. The non-mineral acid may further include, if desired, an organic fatty acid. Such acids may include, for example, butyric, hexanoic, heptanoic, octanoic, nonanoic, decanoic acid or mixtures thereof. The hydrophilic solvent is, for example, water, other hydrophilic solvents such as, for example, propylene glycol, glycerine, polyethylene glycol, and the like, or mixtures thereof.

Cation Sources

There are a large number of possible cation sources useful in the present invention such as for example, alkali metal salts, alkaline earth metal salts, transition metal salts, ammonium cations, protonated amine or amine oxide compounds, or quaternary ammonium compounds. In one embodiment, cation sources include alkali and alkaline earth metal cations with anionic counter ions of iodide, bromide, chloride, sulfate, phosphate, bitartrate, nitrate, citrate, methyl sulfate, alkyl carboxylates, and the like. Typical of these cations are the alkali metals of sodium and potassium. In another embodiment, cation sources include those which are derived from nitrogen sources such as quaternary ammonium, protonated amines, protonated amine oxides and amphoterics, especially with anionic counter ions of iodides, bromides, iodides, sulfates, bitartrate, citrate, and phosphotidyl. Particularly useful of the nitrogen source cations are those derived from choline, betaine, serine, glycine, and the like.

Polymeric cation sources, other than proteins, are not considered viable components of the current composition because of solubility and efficacy issues.

Typically, the quaternary nitrogen compound can be a quaternary ammonium compound having the formula:

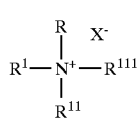

(I)

wherein X is an anion except a hydroperoxide anion; R, $R^1$, $R^{11}$ and $R^{111}$ are each independently a straight or branched, unsaturated or saturated, hydrocarbon group of 1 to 24 carbon atoms, in which the hydrocarbon chain is unsubstituted or substituted by hydroxyl, carboxyl, or alkylamido, or in which the hydrocarbon chain is uninterrupted or interrupted by a heteroatom; an aryl group, or aralkyl group in which alkyl has 1 to 4 carbon atoms, and wherein any two of R, R', R" and R'" taken together with the nitrogen atom form a 5 or 6 membered saturated or unsaturated ring. One embodiment of the formula I includes a compound where $R^1$ is benzyl and $R^{11}$ is aryl or benzyl.

An alkyl group is defined as a paraffinic hydrocarbon group which is derived from an alkane by removing one hydrogen from the formula. The hydrocarbon group may be linear or branched. Simple examples include methyl ($CH_3$) and ethyl ($C_2H_5$). However, in the present invention, at least one alkyl group may be medium or long chain having, for example, 8 to 16 carbon atoms, preferably 12 to 16 carbon atoms.

An alkylamido group is defined as an alkyl group containing an amide functional group: —$CONH_2$, —CONHR, —CONRR'.

A heteroatom is defined as a non-carbon atom which interrupts a carbon chain. Typical heteroatoms include nitrogen, oxygen, phosphorus, and sulfur.

An aryl group is defined as a phenyl or naphthyl group containing 6 to 14 carbon atoms and in which the aromatic ring on the phenyl or naphthyl group may be substituted with a $C_1$–$C_3$ alkyl. An aralkyl group is aryl having an alkyl group of 1 to 4 carbon atoms, e.g. benzyl.

Certain quaternary nitrogen compounds are especially useful. These include substituted alkyl trimethyl ammonium salts, dialkyl dimethyl ammonium salts, dimethyl piperidinium salts, and dimethyl pyridinium salts. Most preferred quaternary nitrogen sources include a choline, particularly choline chloride, choline bitartrate, acetyl choline salts, quaternized starch derivatives; or mixtures thereof. An additional preferred compound is cetyl methyl pyridinium chloride. The nitrogen source may also include mixtures thereof.

The nitrogen compound can also be of the formula:

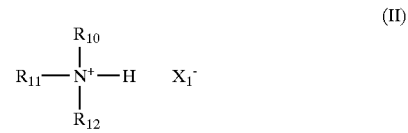

(II)

wherein $X_1$ is an anion; and $R_{10}$, $R_{11}$ and $R_{12}$ are each, independently, hydrogen or at least one straight or branched, saturated or unsaturated, hydrocarbon group of 1 to 24 carbon atoms, in which the hydrocarbon chain is unsubstituted or substituted by hydroxyl, carboxyl, or alkylamido, or in which the hydrocarbon chain is uninterrupted or interrupted by a heteroatom; an aryl group, or aralkyl group in which alkyl has 1 to 4 carbon atoms. Certain protonated nitrogen compounds are especially useful. These include ammonia, morpholine, ethanolamine, and ethylenediaminetetraacetic acid (EDTA) salts.

Several examples of compounds are shown below. The first structure shown is cetyl trimethyl ammonium chloride, which is an example of formula I; the second structure, dodecyl dimethyl ammonium hydrochloride, is an example of formula II, and the third is didecyl dimethyl ammonium chloride, another example of formula I:

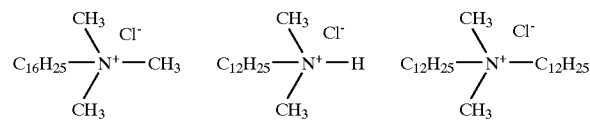

In each structure, the ammonium nitrogen is seen as covalently bonded to four substituents and ionically bonded to a chlorine anion.

In the invention, the quaternary ammonium cation can also be generated from an amphoteric molecule. An amphoteric compound can function as either an acid or as a base, depending on its environment, and has both functional groups present. A representative structure of the cation generated from an amphoteric molecule is shown below:

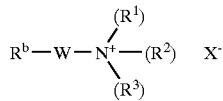
(III)

wherein W is a linear or branched alkyl or alkylene, hydroxyalkylene or alkoxyalkylene group having 1–6 carbon atoms;

$R^b$ is H, $R^4$—CO—NH in which $R^4$ is a saturated or unsaturated, branched or linear hydrocarbon group having 1–22 carbon atoms, or $R^4$;

$R^1$ is hydrogen, A or $(A)_n$—W—$CO_2^-M^+$ in which A is a linear or branched alkyl, hydroxyalkyl or alkoxyalkyl having 1–4 carbon atoms, n is an integer from 0 to 6, and M is an alkali metal cation, a hydrogen ion or an ammonium cation;

$R^2$ is $(A)_n$—W—$CO_2^-M^+$;

$R^3$ is hydrogen or A; and

X is an anion.

A nitrogen compound can also be generated from an amphoteric molecule as shown below:

where R is hydrogen, straight or branched alkyl having 1 to 16 carbon atoms, in which the alkyl group is uninterrupted or interrupted by phenyl. Treatment with an organic or inorganic acid $H^+X^-$ can result in a compound of the formula:

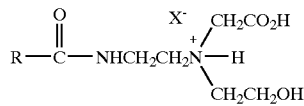

where $X^-$ is an anion. This compound can be mixed with an appropriate oxidant and halogen, or halide salt, to meet the claimed invention.

Another class of amphoteric-like compounds can include the phosphorus containing natural products such as phospholipids like the lecithins (including phosphatidyl choline.), sphingomyelin, and the cephalins. Or modified phospho-amphoterics such as the Phosphoterics®, sold by Mona Industries. Especially useful are various phospholipid derivatives including phosphatidylcholine, phosphatidylinositol, phosphatidylserine, phosphatidylethanolamine, and other phosphatides. The invention can also use protonizable nitrogen sources. Examples include proteins, amino acids, amine oxides and amines which can form acid salts and mixtures thereof. These include, for example, serine, taurine, glycine, and simple proteins such as albumins, phosphoproteins, protamines, histones, chromoproteins, schleroproteins, glutenins and globulins. Examples of protonizable proteins include milk, egg, blood and plant proteins. The nitrogen compound can be a protein, an acid salt thereof, or a mixture of proteins and their corresponding acid salts. Generally, these can be characterized as:

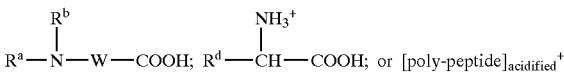

wherein $R^a$ is a linear or branched, saturated or unsaturated, hydrocarbon, hydroxyalkyl or alkoxyalkyl group having 1–22 carbon atoms; $R^b$ is H or $CH_3$, and W is a linear or branched alkylene, hydroxyalkylene or alkoxyalkylene group having 1–4 carbon atoms.

$R^d$ is a common moiety as part of natural amino acids; e.g., H, alkyl, hydroxyalkyl, thioalkyl, alkyl-aryl, carboxyl, amido, alkyl-amino, and the like.

$[\text{poly-peptide}]_{acidified}^+$ refers to an acidified polypeptide, such as an acidified protein.

The nitrogen compound can also be a betaine, sarcosine, sultaine or phosphobetaine of the formula

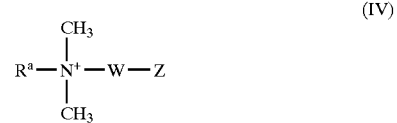
(IV)

wherein Z is $CO_2H$, $CO_2^-$, $SO_3H$, $SO_3^-$, $OSO_3H$, $OSO_3^-$, $OPO_3H$ or $OPO_3^-$; W is a linear or branched alkylene, hydroxyalkylene or alkoxyalkylene group having 1–6 carbon atoms; and $R^a$ is a linear or branched alkyl, hydroxyalkyl or alkoxyalkyl group having 1–22 carbon atoms; or $R^4$—CO—NH $(CH_2)_{x'}$ in which $R^4$ is a saturated or unsaturated, branched or linear hydrocarbon group having 4–22 carbon atoms, and x' is an alkylene group having 1–6 carbon atoms.

A suitable betaine cation is shown below:

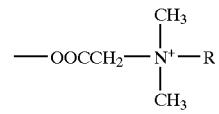

wherein; R is a linear or branched alkyl, hydroxyalkyl or alkoxyalkyl group having 1–22 carbon atoms; or $R^4$—CO—NH(CH)$_x$ in which $R^4$ is a saturated or unsaturated, branched or linear hydrocarbon group having 4–22 carbon atoms, and x is an alkylene group having 1–6 carbon atoms. Of special interest is the natural product betaine where R has 1 carbon atom.

In another embodiment, the nitrogen compound can be of the formula:

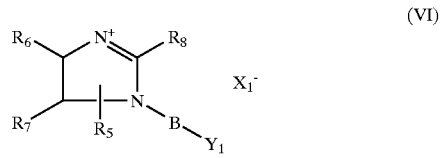
(VI)

wherein $R_6$, $R_7$ and $R_8$ are each, independently, H or —$A_1$—Y in which $A_1$ is a $C_7$ to $C_{20}$ saturated or unsaturated, linear or branched alkylene group, and Y is H, $NH_2$, OH or $COOM_1$ in which $M_1$ is H or a Group I metal ion;

B is a $C_1$ to $C_{20}$ saturated or unsaturated, linear or branched chain alkylene group, and $Y_1$ is H, $NH_2$, OH, $COOM_2$ or —NH—$COR_q$ in which $M_2$ is H or a Group I metal ion and $R_q$ is a $C_1$ to $C_{20}$ saturated or unsaturated, linear or branched chain alkyl group;

$R_5$ is H or a $C_1$ to $C_3$ alkyl group at one of the nitrogen atoms; and $X_1^-$ is an anion.

Typical imidazolines are: coconut hydroxyethyl imidazoline, tall oil aminoethyl imidazoline, oleyl hydroxyethyl imidazoline, the Miramines®, the Rhodaquats®, the Monazolines®, the Rewoterics®, the Crodazolines®, available from Mona Industries Inc., Rhone Poulenc, Rewo Chemische Werke GmbH, and Croda Surfactants Ltd.

Oxidants

In addition to the source of a cation, an oxidizing agent is also necessary. It is possible to utilize oxidants such as hypochlorites (or a counter acid), chlorates, chlorites, bromine, bromates, bromine monochloride, hypobromites (or a counter acid), iodine, iodine monochoride, iodates, permanganates, nitrates, etc.; or gaseous oxidants such as ozone, oxygen, chlorine dioxide, chlorine, sulfur dioxide, etc. One embodiment includes peroxygen compounds which include peroxides and various percarboxylic acids, including percarbonates. Typical peroxygen compounds are hydrogen peroxide, peracetic acid, a persulphate, or a percarbonate. The percarbonate can be formed in situ as a mixture of hydrogen peroxide and sodium bicarbonate. Percarboxylic acids may also be formed in situ by use of a combination of hydrogen peroxide and the desired carboxylic acid. For solid compositions, the use of percarbonates, perborates, persulfates, etc., and $I_2$ are useful; especially where the backbone substrate (e.g., carbonate) itself is not essentially oxidized but instead acts as a substrate for the peroxygen complex. One embodiment employs sodium percarbonate in solid formulations; however, gaseous oxidants such as $Cl_2$, and liquid oxidants such as $I_2$ and $Br_2$ are useful for some compositions. For liquid compositions, typical oxidants useful in the preparation are, for example, a halogen containing oxidizer as $I_2$, $IO_3^-$, ICl, IBr, $IO_4^-$, BrCl, $Cl_2$, $OCl^-$, HOCl, $ClO_2^-$, $ClO_3^-$, $ClO_4^-$, $Br_2$, HOBr, $OBr^-$, $BrO_3^-$, and a mixture thereof. Additionally, for liquids, electrolytic generation of an active species, such as $Cl_2$ or $O_3$ or persulphate, is also possible. Ultimately, any oxidant that can convert the halide source into its complexed form is acceptable.

Halides

There are a large number of possible halide sources useful in the present invention such as metal or ammonium halides, haloforms, other organic halogens, or elemental halogens. Typical metal halides include alkali and alkaline earth metal iodide, bromide, or chloride salts of the formula $MI_n$, $MBr_n$, and $MCl_n$ wherein M is a metal ionic species and n is a number equal to the metal valence. Preferred are the alkali metals of sodium and potassium. Other halides include ammonium or quaternary ammonium iodides, bromides, and iodides. One embodiment uses an alkali metal halide salt which includes a mixture of halide salts containing at least one iodide salt. The alkali metal is preferably sodium or potassium. Another embodiment uses a single metal halide salt which is an iodide or bromide salt. A preferred salt is potassium iodide, sodium iodide, cuprous iodide or a mixture thereof. Also useful are sources containing halides such as sea water, kelp, table salt, etc.

Acids

The invention can also include, if necessary, an acid component for controlling the use solution pH. This may be necessary for non-permanent quaternary ammonium compounds (i.e., amphoteric, amine oxides, amines, proteins, amino acids) to enhance microbial reduction; probably because the unquaternized amine compound must be in its cationic or slightly neutralized form to form the labile, in-situ complex. The exact pH necessary will depend on the identity of the amine involved but, preferably, should be about 9.5 or less, preferably less than about 8.5.

Organic acids are useful for pH adjustment. The acid source might, for example, be an organic-based acid such as malic acid, tartaric acid, citric acid, acetic acid, glycolic, glutamic acid, sorbic acid, benzoic acid, or dimer acids such as oxalic acid, succinic acid, glutaric acid, adipic acid, maleic acid, fumaric acid, etc., or fatty acids such as butyric acid, caprylic acid, caproic acid, octanoic acid, nonanoic acid, decanoic acid, and the like; or mixtures thereof. Organic acids also include organic sulfonic acids, such as arylsulfonic acids, arylethersulfonic acids, alkylarylsulfonic acids. Typically used are xylene sulfonic acid, toluene sulfonic acid, cumene sulfonic acid, and methylsulfonic acid. Alternatively, the source of acidity can include an acid salt such as sodium diacetate, sodium bitartrate, monobasic potassium or sodium phosphate. Additionally, carbonation acidification via the interaction of carbon dioxide with water is possible for aqueous formulations.

Mineral acids are not desirable nor do they form part of the present invention. These include commonly known strong acids such as nitric, phosphonic, hydrochloric, sulfamic, and sulfuric acids.

Besides the aforementioned cationic and amphoteric surfactants for the active complex formation, the invention also includes standard nonionic, anionic, cationic, or amphoteric compounds for surface tension reduction, wetting, and detersiveness. For example, linoleic acid, alkyl glycosides, alcohol ethoxylates, nonylphenol ethoxylates, alkanolamides, alkylbenzene sulfonates, petroleum sulfonates, diphenylether sulfonates, alpha-olefin sulfonates, stearyl citrate, alkyl naphthalene sulfonates, Pluronics® and various short-chain fatty acids are all readily useful. The wetting agents are typically not necessary for affecting the microbial reduction, but are present for detersive and surface tension reduction reasons; however, some may be employed as part of the synergistic, in-situ, antimicrobial formula.

Likewise, inerts might be added as fillers, buffers, chelants, anticaking agents, etc. For example, formulations have been prepared with: sodium chloride, bicarbonates, sulfates, silicates, phosphates, cellulosic derivatives, and EDTA.

It is believed that the working compound in the composition of the invention is a poly-halogen salt of a cation source, which is preferably a quaternary ammonium cation or a combination of a quaternary ammonium cation and an alkali metal cation. The inter- or poly-halogen salt can include an anion of the formula $I_w Br_y Cl_{y1} V_z$, wherein w is an integer from 1 to 8, y and $y_1$ are each independently integers from 0 to 8, and z is an integer from 0 to 1. V is any anion other than a halogen or hydroperoxide. In a typical reaction, for example, a cation, preferably a quaternary ammonium compound, reacts with potassium iodide in the presence of an oxidizing agent to produce the poly-halogen mixed salt of potassium and quaternary ammonium compound. If only KI and a quaternary ammonium iodide are used, the poly-halogen anion is represented by $I_w$, where w ranges from 1 to 8. If KBr is also added to the reaction mixture, the resulting interhalogen anion is represented by $I_w Br_y$, where w plus y equals 2 to 9. If a quaternary ammonium chloride is used the reaction with potassium iodide in the presence of an oxidizing agent would produce an inter-halogen mixed salt; e.g., K $I_w Cl_y$ and quaternary ammonium $I_w Cl_y$, where the sum of w and y are greater than 1. If a quaternary ammonium chloride is used the reaction with potassium iodide and potassium bromide in the presence of an oxidizing agent would produce another interhalogen mixed salt; e.g., K $I_wCl_yBr_z$ and quaternary ammonium $I_wCl_yBr_z$ where the sum of w, y and z are greater than 2. Another mixture would include a quaternary ammonium chloride reacted with potassium iodide in the presence of a stoichiometric amount of chlorine gas as the oxidizing agent. This reaction would produce an inter-halogen mixed salt; e.g., K $I_wCl_y$ and quaternary ammonium $I_wCl_y$ where the sum of w and y are greater than 1. While an inorganic bromide or chloride are optional in the reaction mixture, the inorganic metal or ammonium iodide is not. The product requires the presence of at least some inorganic metal or ammonium or organic iodide. In another typical reaction, for example, to produce a single-cation inter- or polyhalide, a quaternary ammonium halide (a cation and halide source) reacts with ICl (an oxidizing agent) to produce the inter- or poly-halogen quaternary ammonium salt. In yet another typical reaction example, to produce a single-cation inter- or polyhalide, a quaternary ammonium halide (a cation and halide source) reacts with $I_2$ (an oxidizing agent) to produce the inter- or poly-halogen quaternary ammonium salt. A variation of this reaction would include the stoichiometric addition of additional cation and oxidant (chlorine gas) to change the interhalide ratio; e.g., choline-$ClI_2$ (brown colored) converted to choline $ICl_x$ (orange to yellow) where x=2–6. A final example, to produce a single-cation interhalide, uses a quaternary ammonium chloride or non-halide salt (e.g., bitartrate, sulphate, methylsulphate, etc.,) along with a halide source such as ammonium iodide, ICl or $I_2$ and chlorine gas as an oxidant to produce a inter-halogen quaternary ammonium salt (e.g., choline $ICl_x$).

The dilute in-use aqueous solution, made by the addition of water to the liquid concentrate of the invention, is characterized by a light yellow to red color which serves as an indicator of solution effectiveness. As long as the color remains, the solution retains good killing properties. The effective time period is about 50 hours. Generally for unbuffered or non-acidic formulations, as the reaction takes place, the pH of the solution increases from about 5 to about 10. At the same time, the oxidation/reduction potential (ORP) increases accordingly. This is noteworthy since ORP normally is in inversely proportional to pH and, thus, indicates a very active oxidizing species being formed. According to the claimed invention, use solutions are aqueous solutions containing a source of a cation which is preferably a quaternary or protonizable nitrogen ammonium compound, an oxidant which is preferably a halogen containing oxidant or peroxide compound, a metal or ammonium halide and any resulting reaction products. It has been discovered that the preferred ternary molar ratio between the three added ingredients, the cation source, preferably a quaternary or protonizable nitrogen ammonium compound, the oxidant which is preferably a halogen containing oxidant or a peroxygen compound, and the halide source, e.g. metal or ammonium halides, respectively can range from 1:1:1 to 1:5:1 to 1:15:15. An optimal range is 1:3:1 to 1:3:3.

Use solutions are formed by combining, in an aqueous medium, the concentrate consisting of a cation source, especially a quaternary ammonium compound, an oxidant which is preferably a halogen containing oxidant or peroxygen compound and a halide source. The dilution is virtually instantaneous, resulting in a use solution which can be used almost immediately or stored for short periods (<7 days). The use solution can be utilized in any application needing either antimicrobial or oxidizing efficacy.

The invention includes a number of antimicrobial and antiviral methods and processes. The invention can be found in a method of reducing microbial or viral populations on a surface or object; said method including treating said surface or object with use solution from the liquid concentrate of the present invention. In one embodiment, the surface is a clean-in-place (CIP) system, while in another it is one of the many non-CIP surfaces encountered in preparing food (e.g., cutting boards, sinks, ware-wash systems, utensils, counter tops, transport belts, aseptic packaging, boot and hand-wash dip-pans, food storage facilities and anti-spoilage air circulation systems, food refrigeration and coolers, blanchers, food packaging materials, third-sink containers, etc.).

In yet another the surface is in a hospital, environment and are sanitized or disinfected surfaces in surgical, infirmity, birthing, mortuary, and clinical diagnosis, etc., rooms. These surfaces can be those typified as "hard surfaces" (such as walls, floors, bed-pans, etc.,), or woven and non-woven surfaces (such as surgical garments, draperies, bed linens, bandages, etc.,), or patient-care equipment (such as respirators, diagnostic equipment, shunts, body scopes, etc.,), or a plethora of surgical and diagnostic equipment. Also, the medical-related surfaces might be those of medical waste or blood spills. The microbes and viruses are often those which lead to tuberculosis, HIV, hepatitis', herpes', and other human pathogenic or opportunistic entities by physical contact or air transmission. The skin disease in question can be, for example, athletes foot fungus or hairy hoof wart disease. Alternatively, the disease can be a skin or transmittable viral disease such as parvovirus, coxsackie or herpes. The disease can also be a mycobacterial or bacterial type, such as tuberculosis or Legionella.

The invention also includes a method of reducing microbial or viral populations in a body or stream of water including treating said body or stream with an effective amount of the liquid concentrate containing the complex from the in-situ reaction of a source of a cation, an oxidant, and a halide source. The body of water can be a swimming pool or a cooling tower, or can alternatively include food processing waters (e.g., flumes, can warmers, retort waters, third-sink sanitizing, bottle coolers, food sprays and misting systems, etc.,). beverage chillers and warmers, meat chilling or scalding waters, sanitizing gels, food processing antimicrobial garment sprays, and non-to-low-aqueous food preparation lubricants, oils, and rinse additives.

Skin diseases of—or on, or transmittable—mammals can also be treated with the same complex. Especially useful is the treatment of skin diseases on animals, or those which spread via transfer to air or surface substrates, such as diseases from fungi, bacteria and viruses. These spreadable skin diseases can include athletes foot fungus and hairy hoof wart disease, or one of the many organisms leading to Mastitis or other mammalian milking diseases. The disease can be a viral disease such as parvovirus, coxsackie virus, or herpes virus. The disease can also be bacterial, such as *S. aureus, E. coli,* Streptococci, etc., or a Mycobacterium type such as that leading to tuberculosis.

The compositions of the invention can be used in reducing microbes in animal feeds and in animal watering stations, enclosures, in animal veterinarian clinics, animal inspection areas, animal surgical areas. Reductions in human pathogenic microbes on animals can be obtained by applying to said animals use solution derived from the liquid concentrate containing the complex. Finally, the compositions can be used to reduce opportunistic pathogenic microbes on eggs, by applying to said eggs an aqueous solution of an effective amount of the complex; especially chicken eggs.

By way of illustration, typical formulation ranges are:

| Component | Useful Wt-% | Preferred Wt-% | More Preferred Wt-% |
|---|---|---|---|
| cation source | 1–20 | 2–15 | 3–10 |
| oxidant compound | 1–40 | 3–20 | 4–10 |
| halide source | 1–40 | 1–15 | 2–10 |
| acidity source | 0–80 | 0–50 | 0–40 |
| wetting agents | 0–20 | 0–10 | 0–5 |
| inerts | 0–80 | 0–40 | 0–30 |

When used, a total actives concentration ranging from 10 to 100,000 ppm is preferred. Useful product use concentration ranges for sanitizing with a liquid composition are given in the table below:

| Component | Useful (ppm) | Preferred (ppm) | More Preferred (ppm) |
|---|---|---|---|
| cation source | 1–10,000 | 10–5,000 | 20–1,000 |
| oxidant compound | 1–30,000 | 30–15,000 | 50–1,500 |
| acidity source | 0–20,000 | 0–5,000 | 0–1,000 |
| halide source | 1–30,000 | 10–15,000 | 20–1,500 |
| wetting agents | 0–5,000 | 0–500 | 0–100 |
| inerts | 0–50,000 | 0–10,000 | 0–1,000 |

Antimicrobial and Antiviral Treatment

Treatment of inanimate objects can be accomplished by spraying or wiping a use solution onto the object or surface. An object can also be treated via submersion into an adequate supply of the use solution, which is typically an aqueous solution containing a major proportion of water and an effective amount of an antimicrobial or antiviral complex. The use solution can also contain one or more film forming agents to prevent excessively rapid shedding of the treatment solution. Volumes of water, such as those found in swimming pools, water cooling towers and food process and transport streams, can be treated by addition of the liquid concentrate. Addition can take place within the main volume of water, or can occur within a makeup stream of fresh water being added to the main volume.

Skin Treatment

The invention also involves methods of treating skin diseases in, or on, mammals. If a short application is sufficient, a use solution can be sprayed or wiped onto an animal. Alternatively, the animal can be dunked into the use solution. If a longer residence time is required, the use solution can contain one or more film forming agents to slow down shedding of the treatment solution. These same complexes and formulations can also be used to treat non-skin surfaces which might come in contact with the skin surfaces (e.g., bandages, gloves, breathing masks).

The following examples further describe the present invention by way of illustration and are not meant to be limiting thereon.

WORKING EXAMPLE #1

Antimicrobial Composition Using Interhalide Compositions

A non-aqueous interhalide composition was prepared by mixing: a cation and chloride source (choline chloride, 10.0 g), an iodine source ($I_2$, 9.1 g), an organic acid (methylsulfonic acid, 10.0 g) in acetic acid as a solvent (70.9 g). This dark brown mixture (mainly choline $CII_2$) was subjected to an oxidant (chlorine gas) until a steady-state yellow color formed. The UV-visible spectrum of each showed the presence of predominantly another interhalide mixture (choline-$ICl_x$, x=2–4). This non-aqueous formula was diluted to deliver various ppm's of total oxidant (titrated as ppm of $I_2$, column 2) and tested for microbial efficacy against the test organisms *S. aureus* and *E. coli;* with the results shown in Table 1. The results were surprisingly found to yield twice the expected amount of titratable iodine, and each concentration demonstrated the extremely effective biocidal activity with greater than 5-log reduction for all 30-second exposures against both organisms.

TABLE 1

Interhalide Biocide Activity

| Run # | 1 Concentration of Interhalide Formula | 2 Titration ppm ($I_2$) | 3 Log Reduction (*S. aureus*) 30 second | 4 Log Reduction (*E. coli*) 30 second |
|---|---|---|---|---|
| | Non Aqueous Compositions | | | |
| 1 | 10 | 18 | >5.5 | >5.4 |
| 2 | 20 | 49 | >5.5 | >5.4 |
| 3 | 30 | 72 | >5.5 | >5.4 |
| 4 | 50 | 127 | >5.5 | >5.4 |

WORKING EXAMPLE 2

Antimicrobial Compositions Using Interhalide Compositions

Various low-to-non-aqueous interhalide compositions were prepared in a similar fashion to Example 1, but with as shown, a change in some of the actives. Thus, by mixing a chloride source (choline chloride or potassium chloride) along with an oxidative iodine and chloride source (ICl)—in a predominantly acetic acid solvent—and subjecting the mix to an additional oxidant (chlorine gas) until a steady-state yellow color formed. The UV-visible spectrum of each showed the predominant loss in the ICl peak and the presence of an interhalide mixture (choline-$ICl_x$, K—$ICl_x$ x=2–4). The formulations containing a nitrogen source (formulas 1–3, 5) yielded a more stable formulation with none to considerably less solid drop-out than the non-nitrogen formula (4). These formulas were tested for microbial efficacy with the results shown in Example 3.

TABLE 2

Interhalide Compositions

| Additive | Formula 1 (wt %) | Formula 2 (wt %) | Formula 3 (wt %) | Formula 4 (wt %) | Formula 5 (wt %) |
|---|---|---|---|---|---|
| acetic acid | 84.2% | 75.8% | 82.2% | 84.2% | 84.2% |
| choline-Cl | 10.0% | 9.0% | 12.0% | 0.0% | 10.0% |
| ICl | 5.8% | 5.2% | 5.8% | 5.8% | 5.8% |
| water | 0.0% | 10.0% | 0.0% | 0.0% | 0.0% |
| KCl | 0.0% | 0.0% | 0.0% | 2.6% | 0.0% |
| $Cl_2$ gas | to color[1] | to color[1] | to color[1] | to color[2] | to color[1] |

[1]Chlorine gas added until a yellow color formation was constant for 15 seconds and UV showed choline-I—$Cl_x$ interhalide formation.
[2]Chlorine gas added until a yellow color formation was constant for 15 seconds and UV showed potassium-I—$Cl_x$ interhalide formation.

WORKING EXAMPLE #3

Antimicrobial Composition Using Interhalide Compositions

The data of Table 3 presents the biocidal efficacy results for the formulas of Table 2. Each of the non-aqueous formulas (run numbers 1–4), and low-aqueous formula (run number 5), was diluted to deliver 20 ppm total oxidant (titrated as ppm of $I_2$, column 2) and tested, at two time exposures, against the test organisms. The results demonstrate the extremely effective biocidal activity of each formula with greater than 5-log reduction for all 30-second exposures. The non-nitrogen formula-4 (run #3) was both less effective in microbial reduction and yielded considerable, and undesired, solid precipitation from the composition.

TABLE 3

Interhalide Biocides

| Run # | 1<br>Interhalide<br>Formula # | 2<br>Titration<br>ppm ($I_2$) | 3<br>Log Reduction<br>(S. aureus)<br>10 second | 4<br><br><br>30 second | 5<br>Log Reduction<br>(E. coli)<br>10 second | 6<br><br><br>30 second |
|---|---|---|---|---|---|---|
| | | Non Aqueous Compositions | | | | |
| 1 | 1 | 23 | 5.0 | >6.8 | 5.4 | >7.0 |
| 2 | 3 | 23 | 4.3 | >6.8 | 5.2 | >7.0 |
| 3 | 4 | 22 | 3.9 | 5.5 | >7.0 | >7.0 |
| 4 | 5 | 23 | 5.4 | >6.8 | >7.0 | >7.0 |
| | | Low Aqueous Compositions | | | | |
| 5 | 2 | 21 | 4.2 | >6.8 | >7.0 | >7.0 |

WORKING EXAMPLE 4

Antimicrobial Composition Using Interhalide Compositions

A variety of non-to-low-aqueous interhalide compositions were prepared by mixing: a cation source (potassium, choline), an iodine source (KI, choline-$CII_2$, $I_2$), and oxidizing with chlorine gas in acetic acid as a primary solvent. Other additives such as non-aqueous solvents (glycerine, propylene glycol, and lactic acid), organic acidulants (xylene sulfonic acid, fumaric acid, methyl sulfonic acid, octanoic acid, acetic acid, lactic acid), surface active agents (lecithin, octanoic acid), and water effect were tested. Each mixture was subjected to an oxidant (chlorine gas) until a steady-state yellow color formed. The UV-visible spectrum of each showed the presence of an interhalide (cation-$ICl_x$, x=2–4). These formulas are shown in Table 4. Of the 28 formulas prepared, or those from the previous examples, those made using a nitrogen source (run #'s 1–25), and those using an iodo-source of ICl, $I^-$, or $CII_2^-$, gave the best results in terms of minimizing solids dropout and solution stability. Other preferred compositions included those using an organic sulfonic acid or low levels (<40%) or water.

TABLE 4

Low-Aqueous Interhalide Compositions

| | Solvents | | | | | Additives | | Iodo/Halide Source | | | | | Oxidant | Acidulants | | |
|---|---|---|---|---|---|---|---|---|---|---|---|---|---|---|---|---|
| Run # | HOAc[1] | $H_2O$ | PG[2] | GLY[3] | LA[4] | OA[5] | LEC[6] | CC[7] | C-CII2[8] | KCl | KI | $I_2$ | $Cl_2$ | MSA[9] | FA[10] | XSA[11] |
| 1 | 70.9 | 10 | 0 | 0 | 0 | 0 | 0 | 10 | 0 | 0 | 0 | 9.1 | to yellow | 0 | 0 | 0 |
| 2 | 75 | 0 | 0 | 0 | 0 | 0 | 0 | 10 | 0 | 0 | 0 | 15 | to yellow | 0 | 0 | 0 |
| 3 | 78 | 0 | 0 | 0 | 0 | 0 | 0 | 10 | 0 | 0 | 0 | 12 | to yellow | 0 | 0 | 0 |
| 4 | 80.9 | 0 | 0 | 0 | 0 | 0 | 0 | 10 | 0 | 0 | 0 | 9.1 | to yellow | 0 | 0 | 0 |
| 5 | 60.9 | 20 | 0 | 0 | 0 | 0 | 0 | 10 | 0 | 0 | 0 | 9.1 | to yellow | 0 | 0 | 0 |
| 6 | 40.9 | 40 | 0 | 0 | 0 | 0 | 0 | 10 | 0 | 0 | 0 | 9.1 | to yellow | 0 | 0 | 0 |
| 7 | 84.9 | 0 | 0 | 0 | 0 | 0 | 0 | 6 | 0 | 0 | 0 | 9.1 | to yellow | 0 | 0 | 0 |
| 8 | 78.9 | 0 | 0 | 0 | 0 | 0 | 0 | 12 | 0 | 0 | 0 | 9.1 | to yellow | 0 | 0 | 0 |
| 9 | 78.1 | 0 | 0 | 0 | 0 | 0 | 0 | 10 | 0 | 0 | 11.9 | 0 | to yellow | 0 | 0 | 0 |
| 10 | 68.1 | 10 | 0 | 0 | 0 | 0 | 0 | 10 | 0 | 0 | 11.9 | 0 | to yellow | 0 | 0 | 0 |
| 11 | 80.4 | 0 | 0 | 0 | 0 | 0 | 0 | 5.5 | 14.1 | 0 | 0 | 0 | to yellow | 0 | 0 | 0 |
| 12 | 70.4 | 10 | 0 | 0 | 0 | 0 | 0 | 5.5 | 14.1 | 0 | 0 | 0 | to yellow | 0 | 0 | 0 |
| 13 | 60.9 | 0 | 20 | 0 | 0 | 0 | 0 | 10 | 0 | 0 | 0 | 9.1 | to yellow | 0 | 0 | 0 |
| 14 | 50.9 | 10 | 20 | 0 | 0 | 0 | 0 | 10 | 0 | 0 | 0 | 9.1 | to yellow | 0 | 0 | 0 |
| 15 | 30.9 | 10 | 40 | 0 | 0 | 0 | 0 | 10 | 0 | 0 | 0 | 9.1 | to yellow | 0 | 0 | 0 |
| 16 | 60.9 | 0 | 0 | 20 | 0 | 0 | 0 | 10 | 0 | 0 | 0 | 9.1 | to yellow | 0 | 0 | 0 |
| 17 | 50.9 | 10 | 0 | 20 | 0 | 0 | 0 | 10 | 0 | 0 | 0 | 9.1 | to yellow | 0 | 0 | 0 |
| 18 | 60.9 | 0 | 0 | 0 | 20 | 0 | 0 | 10 | 0 | 0 | 0 | 9.1 | to yellow | 0 | 0 | 0 |
| 19 | 75.9 | 0 | 0 | 0 | 0 | 5 | 0 | 10 | 0 | 0 | 0 | 9.1 | to yellow | 0 | 0 | 0 |
| 20 | 65.9 | 10 | 0 | 0 | 0 | 5 | 0 | 10 | 0 | 0 | 0 | 9.1 | to yellow | 0 | 0 | 0 |
| 21 | 65.9 | 10 | 0 | 0 | 0 | 0 | 5 | 10 | 0 | 0 | 0 | 9.1 | to yellow | 0 | 0 | 0 |
| 22 | 65.9 | 10 | 0 | 0 | 0 | 2.5 | 2.5 | 10 | 0 | 0 | 0 | 9.1 | to yellow | 0 | 0 | 0 |
| 23 | 50.9 | 0 | 0 | 0 | 0 | 0 | 0 | 10 | 0 | 0 | 0 | 9.1 | to yellow | 0 | 30 | 0 |
| 24 | 70.9 | 0 | 0 | 0 | 0 | 0 | 0 | 10 | 0 | 0 | 0 | 9.1 | to yellow | 10 | 0 | 0 |
| 25 | 70.9 | 0 | 0 | 0 | 0 | 0 | 0 | 10 | 0 | 0 | 0 | 9.1 | to yellow | 0 | 0 | 10 |
| 26 | 72.7 | 10 | 0 | 0 | 0 | 0 | 0 | 0 | 0 | 5.4 | 11.9 | 0 | to yellow | 0 | 0 | 0 |
| 27 | 62.7 | 20 | 0 | 0 | 0 | 10 | 0 | 0 | 0 | 5.4 | 11.9 | 0 | to yellow | 0 | 0 | 0 |
| 28 | 65.5 | 20 | 0 | 0 | 0 | 0 | 0 | 0 | 0 | 5.4 | 0 | 9.1 | to yellow | 0 | 0 | 0 |

[1]acetic acid
[2]propylene glycol
[3]glycerine
[4]lactic acid
[5]octanoic acid
[6]lecithin
[7]choline chloride
[8]choline $CII_2$
[9]methane sulfonic acid
[10]fumaric acid
[11]xylene sulfonic acid

We claim:

1. An antimicrobial composition concentrate comprising an inter-polyhalide having at least two halide atom types and at least three total halide atoms selected from $ICl_2^-$, $ICl_3^-$, $ICl_4^-$, $IBr_2^-$, $IBr_3^-$, and a mixture thereof, the inter-polyhalide being a reaction product of ingredients which comprise:
   (a) a cation source;
   (b) an oxidant;
   (c) a halide source comprising a metal halide, a halogen, or a mixture thereof, wherein said halide or halogen comprises at least one iodine atom; and
   (d) a non-mineral acid, or a mixture of a non-mineral acid and up to about 50% of a hydrophilic solvent by volume.

2. A composition according to claim 1, wherein the cation is an alkali metal, alkaline earth metal, transition metal, a nitrogen compound selected from an ammonium, quaternary ammonium, and protonizable ammonia compound, or a mixture thereof.

3. A composition according to claim 2, wherein the alkali metal is potassium, sodium or a mixture thereof.

4. A composition according to claim 2, wherein the nitrogen compound is selected from choline, betaine, lecithin, phosphatidylcholine, glycine, serine and a mixture thereof.

5. A composition according to claim 1, wherein the non-mineral acid is selected from acetic acid, malic acid, fumaric acid, maleic acid, glycolic acid, lactic acid, succinic acid, tartaric acid, an organic sulfonic acid, and mixtures thereof.

6. A composition according to claim 5, wherein the organic sulfonic acid is xylene sulfonic acid, toluenebenzene sulfonic acid, or methyl sulfonic acid.

7. A composition according to claim 1, wherein the hydrophilic solvent is water.

8. A composition according to claim 1, wherein the oxidant is $I_2$, $IO_3^-$, $ICl$, $IBr$, $IO_4^-$, $BrCl$, $Cl_2$, $OCl^-$, $HOCl$, $ClO_2^-$, $ClO_3^-$, $ClO_4^-$, $Br_2$, $HOBr$, $OBr^-$, or $BrO_3^-$.

9. A composition according to claim 1, wherein the metal halide is lithium iodide, potassium iodide, sodium iodide, cuprous iodide, lithium chloride, sodium chloride, potassium chloride, or a mixture thereof.

10. A composition according to claim 1, which further comprises inerts, acidulants, and surfactants.

11. A sanitizing composition concentrate comprising an inter-polyhalide having at least two halide atom types and at least three total halide atoms selected from $ICl_2^-$, $ICl_3^-$, $ICl_4^-$, $IBr_2^-$, $IBr_3^-$, and a mixture thereof; the inter-polyhalide being a reaction product of ingredients which comprise:
   (a) a cation source;
   (b) an oxidant selected from $I_2$, $IO_3^-$, $ICl$, $IBr$, $IO_4^-$, $BrCl$, $Cl_2$, $OCl^-$, $HOCl$, $ClO_2^-$, $ClO_3^-$, $ClO_4^-$, $Br_2$, $HOBr$, $OBr^-$, $BrO_3^-$, and a mixture thereof;
   (c) a halide source comprising a metal halide, a halogen or a mixture thereof, wherein said halide or halogen comprises at least one iodine atom; and
   (d) a non-mineral acid, or a mixture of a non-mineral acid and up to about 50% water by volume.

12. A composition according to claim 11, wherein the cation is a quaternary or protonizable nitrogen compound.

13. A composition according to claim 11, wherein the cation is an alkali metal.

14. A composition according to claim 11, wherein the non-mineral acid is selected from acetic acid, malic acid, fumaric acid, maleic acid, glycolic acid, lactic acid, succinic acid, tartaric acid, an organic sulfonic acid, butyric acid, hexanoic acid, heptanoic acid, octanoic acid, nonanoic acid, decanoic acid, and mixtures thereof.

15. A composition according to claim 14, wherein the organic sulfonic acid is xylene sulfonic acid, alkylbenzene sulfonic acid, or methyl sulfonic acid.

16. A composition according to claim 12, wherein the nitrogen compound is selected from choline, betaine, lecithin, glycine, serine, and a mixture thereof.

17. A composition according to claim 11, which further comprises an organic fatty acid.

18. A method of reducing the microbial count on animals or animal carcasses comprising diluting a concentrate composition according to claim 1 with water, and applying a resulting diluted solution to said animals or animal carcasses.

19. A method of reducing microbial population on a surface or object comprising:
   diluting a concentrate composition according to claim 1 with water, and applying a resulting diluted solution to said surface.

20. The method of claim 19, wherein the surface or object is a clean-in-place system, a clean-out-of-place system, a warewash machine, or a sink.

21. The method of claim 19, wherein the surface or object is an aseptic package or device.

22. A method of sanitizing a surface or object comprising applying thereto an antimicrobial effective amount of an inter-polyhalide complex comprising a cation source, and an inter-polyhalide having at least two halide atom types and at least three total halide atoms selected from $ICl_2^-$, $ICl_3^-$, $ICl_4^-$, $IBr_2^-$, $IBr_3^-$, and a mixture thereof.

23. A method of sanitizing a surface or object comprising applying thereto an antimicrobial effective amount of an inter-polyhalide complex comprising a protonated nitrogen compound selected from choline, betaine, lecithin, glycine, serine and a mixture thereof, and an inter-polyhalide having at least tow halide atom types and at least three total halide atoms selected from $ICl_2^-$, $ICl_3^-$, $ICl_4^-$, $IBr_2^-$, $IBr_3^-$, and a mixture thereof.

24. The method of claim 23, wherein the protonated nitrogen compound is choline and the interhalide is selected from $ICl_2^-$, $ICl_3^-$, $ICl_4^-$, and a mixture thereof.

25. The method of claim 22, wherein said complex is applied by first diluting with water a liquid concentrate comprising said complex and a non-mineral acid or a mixture of a non-mineral acid and up to 40% of a hydrophilic solvent by volume.

26. The method of claim 25, wherein the non-mineral acid is selected from acetic acid, malic acid, fumaric acid, maleic acid, glycolic acid, lactic acid, succinic acid, tartaric acid, an organic sulfonic acid, butyric acid, hexanoic acid, heptanoic acid, octanoic acid, nonanoic acid, decanoic acid, and mixtures thereof.

27. The method of claim 25, wherein the hydrophilic solvent is water.

28. The method of claim 23, wherein said complex is applied by first diluting with water a liquid concentrate comprising said complex and a non-mineral acid or a mixture of a non-mineral acid and up to 40% of a hydrophilic solvent by volume.

29. The method of claim 23, wherein the non-mineral acid is selected from acetic acid, malic acid, fumaric acid, maleic acid, glycolic acid, lactic acid, succinic acid, tartaric acid, an organic sulfonic acid, butyric acid, hexanoic acid, heptanoic acid, octanoic acid, nonanoic acid, decanoic acid, and mixtures thereof.

30. The method of claim 23, wherein the hydrophilic solvent is water.

31. A method of sanitizing a surface or object comprising:
(a) diluting with water a liquid concentrate composition comprising an antimicrobial effective amount of an inter-polyhalide complex comprising protonated choline and an inter-polyhalide having at least two halide atom types and at least three total halide atoms selected from $ICl_2^-$, $ICl_3^-$, $ICl_4^-$, $IBr_2^-$, $IBr_3^-$, and a mixture thereof, in acetic acid or a mixture of acetic acid and up to 40% water by volume; and
(b) applying the diluted liquid concentrate composition to the surface or object.

32. A method of reducing the microbial count on animals or animal carcasses comprising applying thereto an antimicrobial effective amount of a complex comprising a protonated nitrogen compound selected from choline, betaine, lecithin, glycine and a mixture thereof, and an inter-polyhalide having at least two halide atom types and at least three total halide atoms selected from $ICl_2^-$, $ICl_3^-$, $ICl_4^-$, $IBr_2^-$, $IBr_3^-$ and a mixture thereof.

33. The method of claim 31, wherein the protonated nitrogen compound is choline and the inter-polyhalide is selected from $ICl_2^-$, $ICl_3^-$, $ICl_4^-$ and a mixture thereof.

34. The method of claim 31, wherein said complex is applied by first diluting with water a liquid concentrate comprising said complex and acetic acid or a mixture of acetic acid and up to 40% water by volume.

35. A method of reducing the microbial count on animals or animal carcasses comprising diluting with water a liquid concentrate composition comprising an antimicrobial effective amount of a complex comprising protonated choline and an inter-polyhalide having at least two halide atom types and at least three total halide atoms selected from $ICl_2^-$, $ICl_3^-$, $ICl_4^-$ and a mixture thereof, in acetic acid or a mixture of acetic acid and up to 40% water by volume, and applying the resulting diluted solution to said animals or animal carcasses.

36. An antimicrobial composition comprising:
(a) an inter-polyhalide complex comprising an inter-polyhalide having at least two halide atom types and at least three total halide atoms, the complex resulting from an in-situ reaction of:
(i) a cation source;
(ii) an oxidant;
(iii) a halide source containing at least one iodine atom, and
(b) a non-mineral acid, or a mixture of a non-mineral acid and up to about 50% of a hydrophilic solvent by volume.

37. The composition of claim 36, wherein the cation source is an alkali metal, a quaternary or protonizable nitrogen compound, or a mixture thereof.

38. The composition of claim 36, wherein the oxidant is selected from ICl, $ICl_2^-$, $ICl_3^-$, $ICl_4^-$, BrCl, $IBr_2^-$, $IBr_3^-$ and a mixture thereof.

39. The composition of claim 36, wherein the hydrophilic solvent is water.

40. The composition of claim 36, wherein the non-mineral acid is acetic acid or a mixture of acetic acid and an organic sulfonic acid.

41. An antimicrobial composition comprising:
(a) a complex comprising:
(i) a nitrogen compound selected from choline, betaine, lecithin, glycine, serine, an alkali metal, and a mixture thereof, and
(ii) an inter-polyhalide having at least two halide atom types and at least three total halide atoms selected from $ICl_2^-$, $ICl_3^-$, $ICl_4^-$, $IBr_2^-$, $IBr_3^-$ and a mixture thereof, and
(b) acetic acid or a mixture of acetic acid and an organic sulfonic acid, and up to 40% water.

42. An antimicrobial composition comprising:
(a) a complex comprising:
(ii) protonated choline; and
(ii) an inter-polyhalide having at least two halide atom types and at least three total halide atoms selected from $ICl_2^-$, $ICl_3^-$, $ICl_4^-$, $IBr_2^-$, $IBr_3^-$, and
(b) acetic acid, or a mixture of acetic acid and up to 40% water by volume.

* * * * *